(12) United States Patent
Marcovici et al.

(10) Patent No.: US 6,292,529 B1
(45) Date of Patent: Sep. 18, 2001

(54) TWO-DIMENSIONAL X-RAY DETECTOR ARRAY FOR CT APPLICATIONS

(75) Inventors: Sorin Marcovici, Lexington, MA (US); Alexander T. Botka, Underhill, VT (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 09/461,892

(22) Filed: Dec. 15, 1999

(51) Int. Cl.⁷ .................................................. G01N 23/00
(52) U.S. Cl. ......................................... 378/19; 250/370.11
(58) Field of Search .................. 378/19; 250/370.09, 250/370.11, 367; 348/162

(56) References Cited

U.S. PATENT DOCUMENTS

| | | |
|---|---|---|
| 3,936,645 | 2/1976 | Iversen ................................. 250/486 |
| 4,338,521 | 7/1982 | Shaw et al. ............................ 250/366 |
| 4,759,047 | 7/1988 | Donges et al. .......................... 378/57 |
| 4,884,289 | 11/1989 | Glockmann et al. .................... 378/57 |
| 4,914,301 | 4/1990 | Akai ................................. 250/370.01 |
| 4,982,096 | 1/1991 | Fujii et al. ............................. 250/367 |
| 5,059,800 | 10/1991 | Cueman et al. ...................... 250/367 |
| 5,151,588 | 9/1992 | Kiri et al. ........................... 250/208.1 |
| 5,247,561 | 9/1993 | Kotowski ................................. 378/87 |
| 5,293,416 | 3/1994 | Pfeiler et al. ........................... 378/146 |
| 5,319,547 | 6/1994 | Krug et al. ............................. 364/409 |
| 5,319,693 | 6/1994 | Eberhard et al. ....................... 378/19 |
| 5,355,309 | 10/1994 | Eberhard et al. ............... 364/413.15 |
| 5,367,552 | 11/1994 | Peschmann ............................ 378/57 |
| 5,390,226 | 2/1995 | Tam ......................................... 378/19 |
| 5,473,658 | 12/1995 | Wallschlaeger ......................... 378/15 |
| 5,490,218 | 2/1996 | Krug et al. ............................. 382/100 |
| 5,510,622 | 4/1996 | Hu et al. ................................ 250/367 |

FOREIGN PATENT DOCUMENTS

| | | | |
|---|---|---|---|
| 0 715 830 | 12/1996 | (EP) | ................................ A61B/6/03 |

Primary Examiner—Robert H. Kim
Assistant Examiner—Courtney Thomas
(74) Attorney, Agent, or Firm—McDermott, Will & Emery

(57) ABSTRACT

An X-ray detector used in CT scanner systems includes a 2-D array of scintillator elements coupled to an improved 2-D array of photo-detectors. When coupled together, each scintillator element aligns with a detection side of a corresponding photo-detector. The photo-detector array includes an insulating substrate which houses and secures the photodiodes in a predetermined alignment with the scintillator elements. The insulating substrate is comprised of a bottom piece and a top piece, wherein the bottom piece has circuit paths formed in a mounting surface thereof. The top piece has a top and a bottom surface, includes photo-detector holes for insertion of the photo-detectors, and has a thickness which is greater than the height of the photo-detectors. Additionally, the top piece includes plated conductive holes which extend from the top surface to conductive pads on the bottom surface and conductive paths formed at the top surface which electrically couple the conductive holes to the photo-detector. The top and bottom pieces are coupled together and then the photo-detectors are countersunk within the photo-detector holes, leaving a detection side of each photo-detector exposed. The detection side of each photo-detector is electrically coupled to a corresponding pair of conductive holes, which creates an electrical path from the detection side of the photo-detector to the circuit path of the bottom piece. The array of scintillator elements, including an alignment grid, is then coupled to the photo-detector array to form a 2-D X-ray detector.

35 Claims, 6 Drawing Sheets

TWO-DIMENSIONAL X-RAY DETECTOR ARRAY FOR CT APPLICATIONS

BACKGROUND OF THE INVENTION

The present invention relates generally to the field of detector arrays and more specifically to the field of X-ray detector arrays in CT scanner applications.

Computed tomography (CT) X-ray scanners are used in a variety of applications. For example, such scanners are used in X-rays in medical diagnostic applications and for X-ray baggage inspection in airport security systems. For the most part, a CT scanner includes at least one X-ray source and a series of X-ray detectors. The detectors are disposed diametrically opposite the X-ray source on a rotating disk. During rotation the X-ray source emits X-rays which pass through the object being scanned and ultimately impinge on the detectors. Given that the original signal characteristics of the emitted X-rays are known, by measuring the attenuated signals arriving at the detectors, the electronics determines the density distribution in the object. Algorithms for determining an object's density based on such signal measurements are well known in the art.

In most CT systems, the X-ray detectors each first translate the received X-ray signal into an optical signal and then translate the optical signal into an electrical signal, which is processed by electronics forming part of each system. The electronics then process the electrical signals in accordance with specific application algorithms. A detector of this type often is made of a light emitting scintillating element (e.g., a scintillator crystal) paired with an optical detector or "photo-detector" (e.g., a photodiode). The scintillator crystal receives the X-ray signal and responsively generates an optical signal (e.g., blue light). The optical signal from each crystal is then detected by its corresponding photodiode, which responsively generates an electrical signal that is a function of the original X-ray flux received by the scintillator crystal. A typical detector array takes the form of a two-dimensional (i.e., m×n) array of detectors, or m×n scintillator crystal and photodiode pairs. It is important in such a detector array that light emitted from one scintillator crystal is not sensed by adjacent photodiodes which are adjacent to the intended photodiode with which the light emitting scintillator crystal is paired. Such light leakage, referred to as "optical cross-talk", causes inaccuracies in the measurement (e.g., noisy signals, erroneous detections by adjacent detectors, artifacts, etc.) and, therefore, in the X-ray system overall.

One X-ray detector array of the prior art is described in pending U.S. patent application Ser. No. 08/948450, assigned to Analogic Corporation of Peabody, Mass. and incorporated herein by reference. As shown in FIGS. 1–4 of the present application, the prior art X-ray detector system includes a large number of relatively small individual detector elements, or scintillator crystal/photodiode pairs, arranged in a two-dimensional (2-D) array. The detector array incorporates a multi-functional structure comprising a set of alignment grids which function both to align each individual scintillator crystal with a corresponding photodiode and also to isolate the individual photodiode/crystal pairs from one another to prevent optical cross-talk. Overall, the detector array is substantially stable under the typical operating conditions of the CT scanning system, which include vibration and/or temperature fluctuations.

As illustrated schematically in FIG. 1, a substrate 12 provides the basic structural support of the prior art detector array. Photodiodes 14 are arranged on the substrate in a 2-D array. As an example, a single m×n array may comprise 72 photodiodes arranged in six rows of twelve photodiodes each (i.e., a 6×12 array). The substrate 12 also includes a signal transmission arrangement 16 for transmitting electrical signals generated by the photodiodes to a signal processing subsystem 20 for image reconstruction. The signal transmission arrangement 16 can include electrically conductive circuit paths printed into the substrate, or an electrically conductive interconnect layer 17 attached to the substrate. Electrically conductive leads 19 from each photodiode to one or more of the paths complete an electrical connection between each photodiode and the signal processing means 20.

A scintillator crystal assembly 18 is positioned over the photodiode array and includes a number of scintillator crystals 22 and alignment grids for arranging the crystals in a 2-D array which corresponds to the photodiode array. Each of the scintillator crystals 22 is substantially aligned and interfaced with a corresponding photodiode 14 and is also substantially optically isolated from surrounding crystals. As shown in FIG. 2, at least one of the alignment grids 24 is substantially planar and includes a number of cells or openings 26. Each of the cells 26 is of a sufficient dimension to receive and substantially align with a scintillator crystal 22, as shown in FIG. 3. Another alignment grid 28 is optically opaque and substantially rigid 2-D grid, having a significant thickness relative to grid 24. It also includes a number of cells 26' corresponding to the cells of the first alignment grid 24. Each of the cells of the alignment grid 28 is substantially aligned with a corresponding cell of the planar alignment grid 24 and thus with a scintillator crystal 22. Optical opacity and dimensional stability are critical features of the alignment grids.

The alignment grids 24 and 28 provide a structural framework for the scintillator crystals 22 in the detector array which ensures the correct alignment of the crystals with corresponding photodiodes 14 and provides dimensional stability to the crystal assembly. As shown in FIGS. 2 and 3, the cells 26, 26' of the respective alignment grids 24, 28 are each sized to accommodate and align a single scintillator crystal with a corresponding photodiode 14. The 2-D alignment grid 28 includes walls which extend above the photodiode array and electrical interconnections 17 on the substrate. The walls are positioned directly in between photodiode detectors and establish individual wells or cells for each scintillator crystal.

The cell width of the 2-D grid is sufficiently large to accommodate the bonding of wire 19 from the detection side of photodiode 14, the traversal of the wire 19 down the side of the photodiode, and bonding of the wire to the electrical layer 17. Because the wire leads 19 from the photodiodes may be relatively fragile, effort is taken to protect them from damage. The 2-D alignment grid 28 additionally serves as a standoff between the photodiode array and a support for the scintillator crystal assembly so that the crystals 22 cannot rest directly on corresponding underlying photodiodes 14 and wire leads 19, which would likely cause damage to the relatively fragile wire leads 19. Therefore, the height and width of grid 28 is at least as great as the height and width of the combined photodiode 14 and wire lead 19, as shown in FIG. 4.

As is also shown in FIG. 4, the scintillator crystals 22 are surrounded on all sides, other than the side closest to a corresponding photodiode 14, by an optically reflective material 30, like paint, foil, or surface deposition layers. The region between a scintillator crystal 22 and a corresponding photodiode 14 is filled with an optically transmissible medium 34 (e.g., epoxy) to facilitate transmission of light from the crystal to the photodiode.

As will be appreciated by those skilled in the art, manufacture of the prior art X-ray detector array tends to be complex and labor intensive, due to the precautions necessary to insure its reliable construction. For example, each wire 19 must be bonded to the photodiode, and carefully looped, such that the wire when bonded to a circuit path on the substrate 12 does not touch the photodiode wall or grid 28. Additionally, alignment grid 28 is itself fragile and vulnerable to breakage, given that grid 28 tends to be made of a brittle material such as glass or ceramic. Also, the loop of wire 19 from the top of photodiode 14 makes the wire vulnerable to damage or displacement and requires that the scintillator crystal array be sufficiently raised above the photodiode array to provide clearance for the wire. Such separation increases the likelihood of optical cross-talk and, thus, might impact the accuracy of the X-ray system overall. Additionally, to compensate for the traversal of wire 19 along the side of the photodiode as it makes its way to the substrate 12, the grid 28 must be precisely fitted to the photodiode array. The errors in fitting might compromise the physical integrity of the photodiode or wire bonding.

Therefore, it is an object of the present invention to provide a 2-D photo-detector array with reduced optical cross-talk, improved structural integrity, and a simplified structure leading to lower manufacturing costs. It is a further object of the invention to provide an improved X-ray detector having greater accuracy, durability, and reliability, which is substantially less costly to manufacture than prior art X-ray detectors. And, it is yet another object of the present invention to provide an improved CT X-ray scanner system which achieves these same benefits.

SUMMARY OF THE INVENTION

The present invention is a 2-D X-ray detector array comprised of an array of scintillator elements (e.g., crystals) coupled to an array of photo-detectors (e.g., photodiodes). When the scintillator crystal array and photodiode array are coupled together, each scintillator crystal is optically coupled to a corresponding photodiode, to form a crystal/photodiode pair. Each scintillator crystal emits light in response to the incidence of X-rays thereon, wherein the emitted light is proportional to the incident X-ray flux. Accordingly, each photodiode detects the light emitted from its corresponding scintillator crystal and produces electrical signals proportional to the received light and, therefore, the original incident X-ray flux. Electrical signals produced by the photodiode array are processed by electronics to determine, among other things, the density distribution in the object through which the X-rays passed when propagating from the X-ray source to the 2-D X-ray detector array.

The scintillator crystals are arranged in an m×n (i.e., 2-D) array and are supported by an m×n grid for alignment, which is known in the art. The photodiodes are also arranged in an m×n array such that each scintillator crystal aligns with a single photodiode when the two arrays are coupled together. Each photodiode includes a detection side that receives light from a scintillator crystal and a mounting side by which the photodiode is mounted onto an insulating substrate.

The insulating substrate and photodiodes are assembled together to form the photodiode array, wherein the insulating substrate includes a top and a bottom insulating piece bonded together and at least two electrical paths corresponding to each photodiode. The bottom insulating piece may be made of a single or multi-layer ceramic or other printed circuit board material. The bottom piece serves as a basic support structure for the X-ray detector array and has a mounting surface with circuit paths formed therein. The circuit paths terminate at bonding pads which are ultimately bonded to a multi-wire flex cable that carries electrical signals from the photodiodes to the electronics. The top piece, which is not known in the art, is constructed to define an array of m×n photodiode holes separated by ceramic walls (or other optically opaque material). The top piece provides physical security and electrical and optical isolation of the photodiodes, as well as increased structural support to the overall substrate. As such, the top piece is an elegant adapter to the known bottom piece to form an improved photodiode array.

The insulating substrate of the photodiode array is formed by fusing the bottom surface of the top piece to the mounting surface of the bottom piece, such that the contact pads at the bottom surface of the top piece are electrically coupled to the circuit paths on the mounting side of the bottom piece and the bonding pads of its surface remain accessible. Once the two ceramic pieces are bonded together, the photodiodes are mounted within the top piece photodiode holes such that the mounting side of each photodiode is coupled to the mounting surface of the bottom piece and the detection side of each photodiode is left exposed to its corresponding scintillator crystal.

Within the ceramic walls of the top piece, conductive holes are formed. Each hole provides a separate electrically conductive path from the top surface of the top piece to a conductive pad at the bottom surface of the top piece. Additionally, for each photodiode, two conductive paths at the top surface of the top piece electrically couple the photodiode to its corresponding conductive holes. When a photodiode is mounted within a detector hole, it is electrically coupled to the conductive paths with a conductive connection, for example, a conductive epoxy or wire. Together, the conductive connections, top surface conductive paths, conductive holes, and conductive pads allow the detection side of the photodiode to be electrically coupled to a circuit path at the bottom piece. Therefore, the need for a fragile looped metal wire, as in prior art, is obviated by the present invention.

The physical structure of the photodiode array is such that improved signal detection accuracy is achieved (i.e., less cross-talk) by the X-ray detector array along with increased structural support. Toward these ends, it is important that the height (or thickness) of the top piece of the substrate be slightly greater than the height of a photodiode and that the top piece to provide an electrical path from the detection side of the photodiode to the bottom piece of the substrate. Countersinking the photodiode within the optically opaque top piece provides improved optical isolation between crystal/photodiode pairs. Additionally, since the wire, which required clearance along the side of the photodiode in the prior art, is routed down to the diode through the top piece walls, the detector holes of the top piece may be smaller in dimension than the glass grid openings used in the prior art. Given that in the present invention the photodiodes may be mounted in smaller, deeper detector holes, they are better separated and more physically secure than in the prior art 2-D X-ray detector array. A tight fit also allows more dependable and secure alignment methodology of the scintillator crystals with the photodiodes.

An additional benefit of the present invention is that manufacturing is significantly simplified, and thus manufacturing costs are reduced. For example, elimination of the fragile and costly glass alignment grid within the diode array reduces costs associated with manufacturing the grid and with losses due to grid breakage or assembly errors. Also, elimination of the long top-down wire bonding significantly reduces the labor and cost associated with bonding a first end of the wire to the detection side of the photodiode, looping the wire, and then bonding a second end of the wire to a circuit path on the bottom piece. Furthermore, the elimination of fragile components increases the durability and reliability of the 2-D X-ray detector array.

BRIEF DESCRIPTION OF THE DRAWINGS

The foregoing and other objects of this invention, the various features thereof, as well as the invention itself, may be more fully understood from the following description, when read together with the accompanying drawings, as described below.

As will be evident when referring to the figures, when an item is used unchanged in multiple figures it retains the same identifying number in those figures.

DETAILED DESCRIPTION OF THE PREFERRED EMBODIMENT

The present invention is a two-dimensional (2-D) X-ray detector array comprised of an array of scintillator elements coupled to an array of photo-detectors. The dimensions of the array of scintillator elements are essentially identical to the dimensions of the array of photo-detectors, wherein the dimensions are indicative of the number of scintillator elements and photo-detectors in the respective arrays. As in the prior art, when the arrays are coupled together each scintillator element aligns with a corresponding photo-detector. In the preferred embodiment of the present invention, the scintillator elements are scintillator crystals and the photo-detectors are photodiodes, such as those described with respect to the prior art illustration FIGS. 1–4. However, other types of scintillator elements may also be used, such as scintillating ceramics or direct conversion materials, like Cadmium Telluride and Selenium. Also, other types of photo-detectors may be used, such as charge-coupled devices, or monocrystalline and amorphous silicon devices. As described with respect to the preferred embodiment, the structure of the photodiode array of the present invention varies significantly from that previously described.

The photodiode array of the present invention is comprised of an insulating substrate having photodiodes mounted therein. The insulating substrate includes top and bottom pieces which are assembled together to provide alignment, structural support, and optical insulation of the photodiodes and scintillator crystals. In the preferred embodiment, the bottom piece is substantially the same as substrate 12 of the prior art. That is, it is made substantially of insulating material and includes circuit paths formed within or proximate to a mounting surface, for accommodating the transmission of electrical signals from the photodiodes to electronics. Suitable materials for the bottom piece include printed circuit board (PCB) material, glass, fiberglass, and ceramics.

Figure 1:
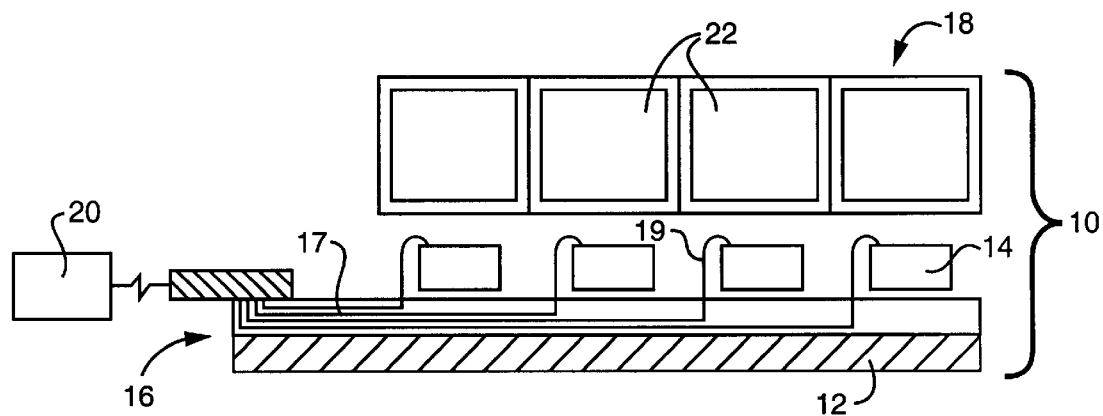
FIG. 1 is a simplified side view of an X-ray detector array of the prior art.
Figure 2:
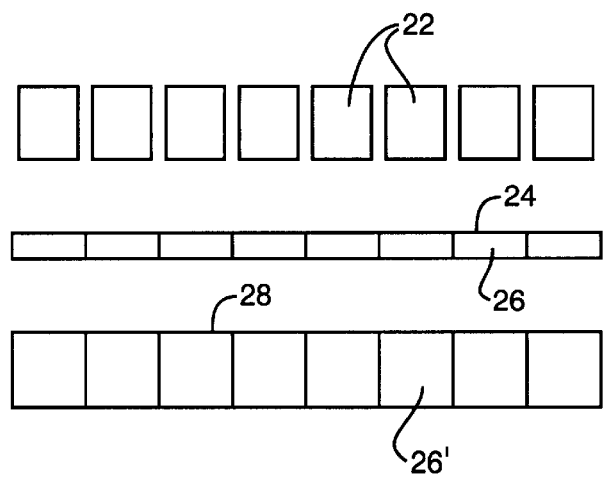
FIG. 2 is a simplified side view of a scintillator crystal assembly of the X-ray detector array of FIG. 1.
Figure 3:
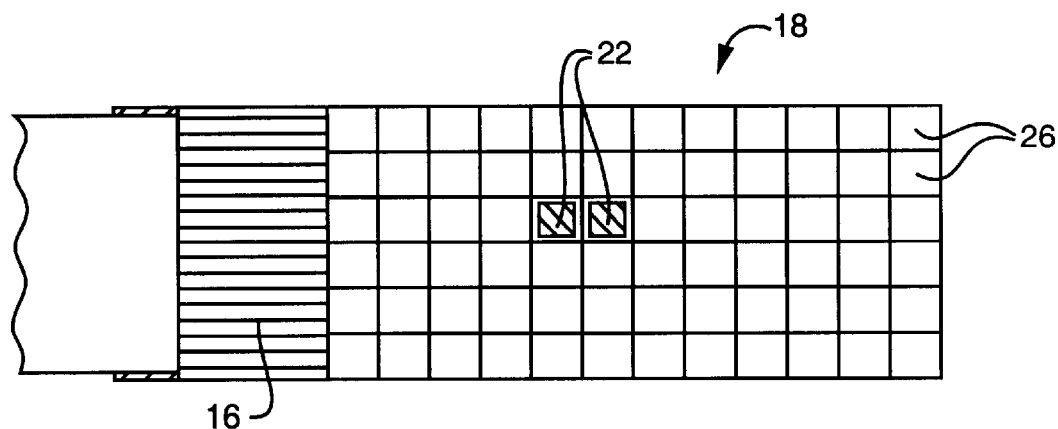
FIG. 3 is a simplified plan view of a portion of the X-ray detector array of FIG. 1.
Figure 4:
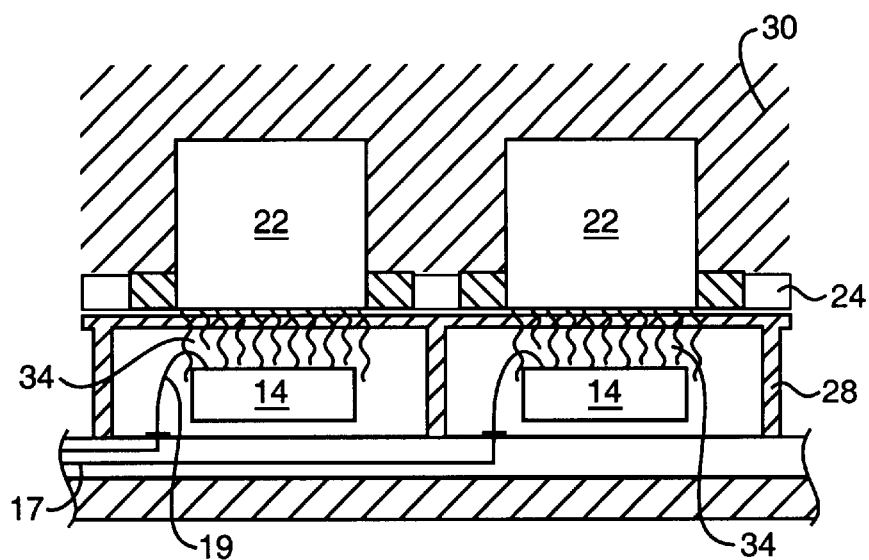
FIG. 4 is a simplified assembled view of a portion of the X-ray detector array of FIG. 1.
Figure 5:
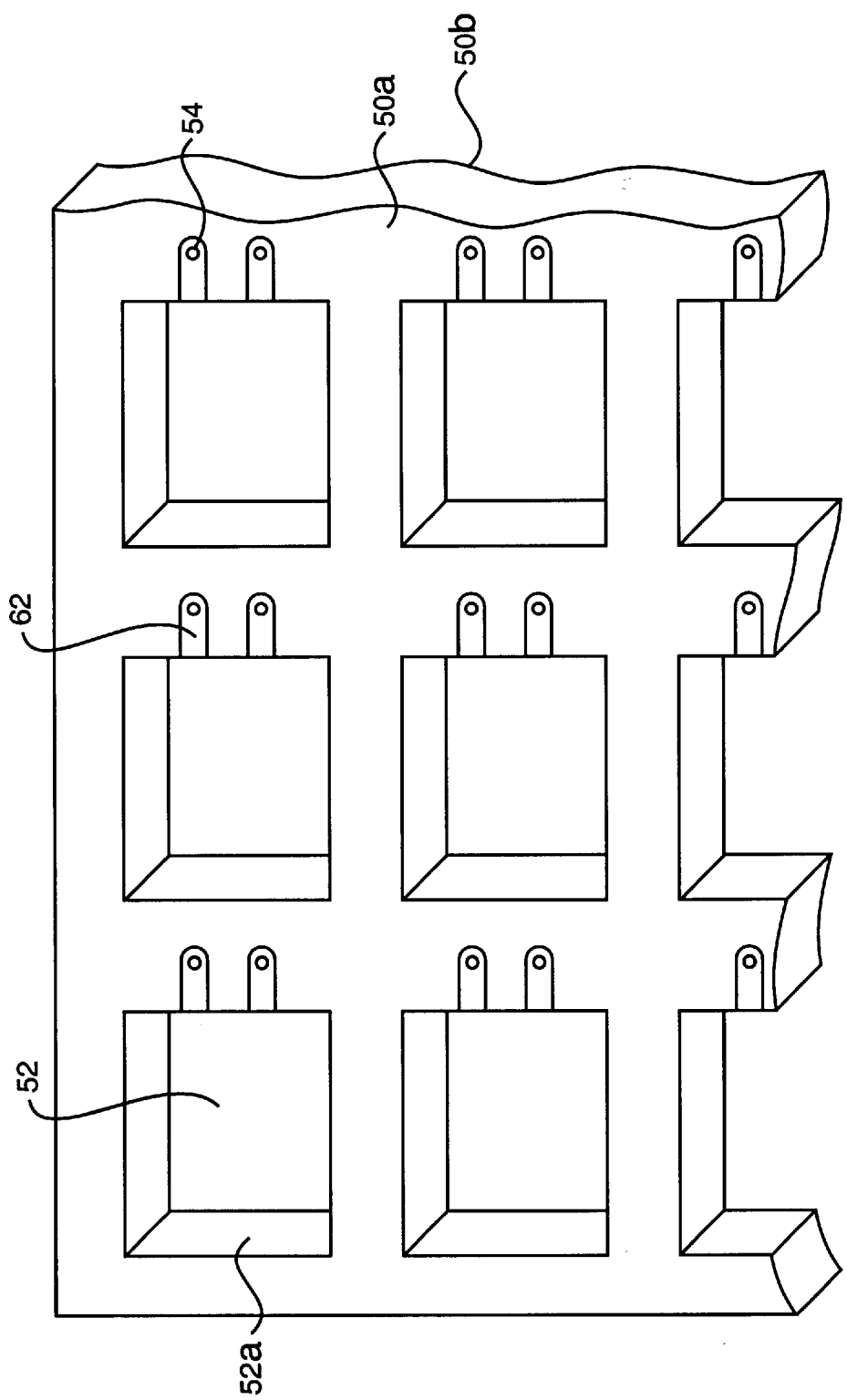
FIG. 5 is a perspective view of a top piece of an insulating substrate of a photodiode array, in accordance with the present invention.

In the preferred embodiment, the top piece 50, shown in FIG. 5, is a rigid structure that has a height (or thickness) which is greater than the height of a photodiode. As will be discussed in greater detail, the height of top piece 50 is chosen to allow a photodiode to be countersunk therein to provide improved optical isolation and is made from an optically opaque material, such as ceramic, PCB material, or glass. The top piece is suited for use with the bottom piece of the prior art, and thus provides an elegant approach to achieving an improved X-ray detector. In other embodiments, the form of the top piece may be varied, particularly to accommodate bottom pieces of different forms, but in all cases the photodiodes are countersunk.

Referring once again to FIG. 5, the top piece includes a top surface 50a that provides an interface to the scintillator crystal array and a bottom surface 50b that mounts to the mounting surface of bottom piece 12. Formed within the top piece 50 and extending from the top surface 50a to the bottom surface 50b is an array of photodiode holes 52 which accommodate insertion of photodiodes. Photodiode holes 52 are defined by walls 52a and are sized to accomplish a relatively close fit with inserted photodiodes 14, shown in FIGS. 6, 7, and 8. Additionally, conductive holes 54 are formed in the top piece 50 and extend from the top surface 50a to corresponding conductive hole pads 66 (shown in FIGS. 6, 7, and 8) formed at the bottom surface 50b of top piece 50. Also, for each photodiode, two conductive paths 62 are formed at the top surface 50a of the top piece 50 and electrically couple the photodiode mounted in the hole 52 to a corresponding conductive hole 54. As examples, a conductive hole may be a hole plated with a conductive material or filled with a conductive epoxy, or some combination thereof.

Figure 6:
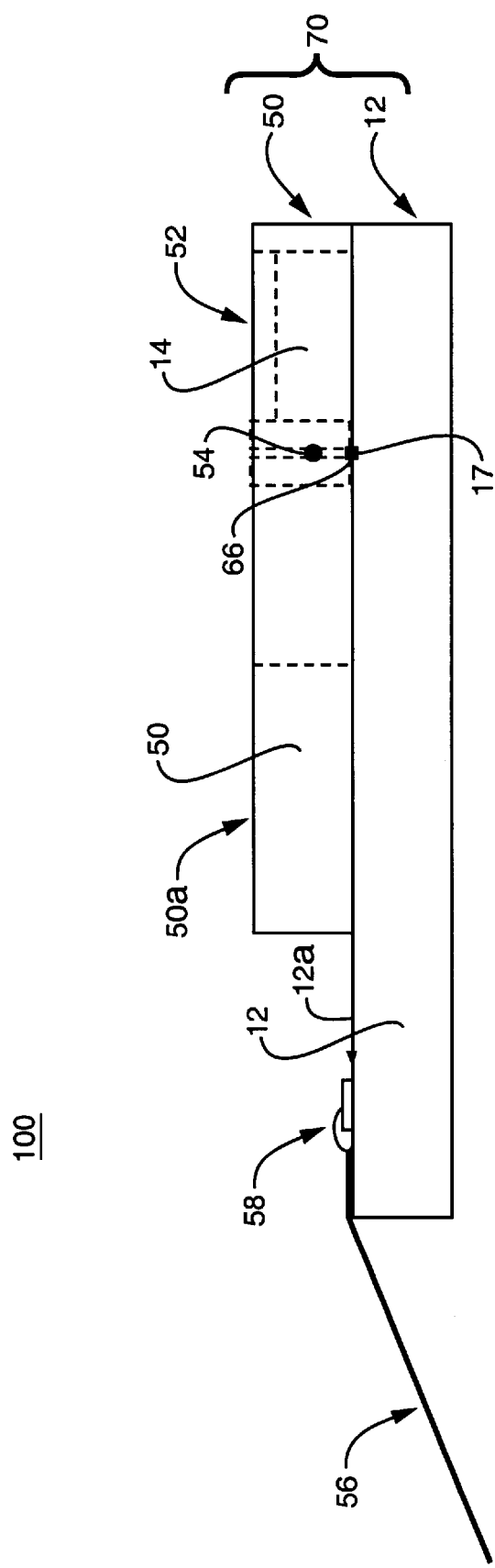
FIG. 6 is a simplified side view of a photodiode array, in accordance with the present invention, including the top piece of FIG. 5.

FIG. 6 shows a cross-sectional view of a photodiode array 100 in accordance with the present invention. Insulating substrate 70 is formed by coupling the top 50 and the bottom 12 pieces. As is shown, when the top and bottom pieces 12 and 50 are coupled together, the top piece is smaller than the bottom piece so that some portion of the mounting surface 12a of the bottom piece 12 is not in contact with the bottom surface 50a of top piece 50. This exposed portion of the mounting surface 12a includes bonding pads 58 which are electrically connected to separate circuit paths 17 in bottom piece 12 and are also bonded to a multi-wire flex cable 56. Bonding pads 58 and flex cable 56 provide transmission paths to signal processing electronics (not shown) for the electrical signals generated by photodiodes 14 and supplied to the circuit paths 17. As will be appreciated by those skilled in the art, other approaches to coupling the signals from circuit paths 17 to another signal transmission medium may also be used and it is not imperative that circuit paths 17 and cable 56 be coupled at the mounting surface of bottom piece 12 or that the top and bottom pieces be different sizes. For example, the circuit paths could terminate at other surfaces of the bottom piece 12 or be coupled to cable 56 through the top piece 50.

To facilitate tight coupling between the two pieces 12 and 50 in forming insulating substrate 70, the mounting surface 12a of the bottom piece 12 and the bottom surface 50b of the top piece 50 are flat in the preferred embodiment. However, it is not critical that each surface be flat, but rather that the mounting surface 12a and the bottom surface 50b have substantially complementary contours such that a tight bond can be formed between the two pieces 12 and 50. Using the preferred materials for pieces 12 and 50, such as ceramic or opaque glass, the pieces are fused together to form a single rigid structure, i.e., insulating substrate 70. Consequently, conductive hole pads 66 on the bottom surface of top piece 50 become electrically coupled to the circuit paths 17 in bottom piece 12. Once the top and bottom pieces are fused together, the photodiodes are then inserted into the photodiode holes 52 and glued to the mounting surface 12a of the bottom piece 12.

Figure 7:
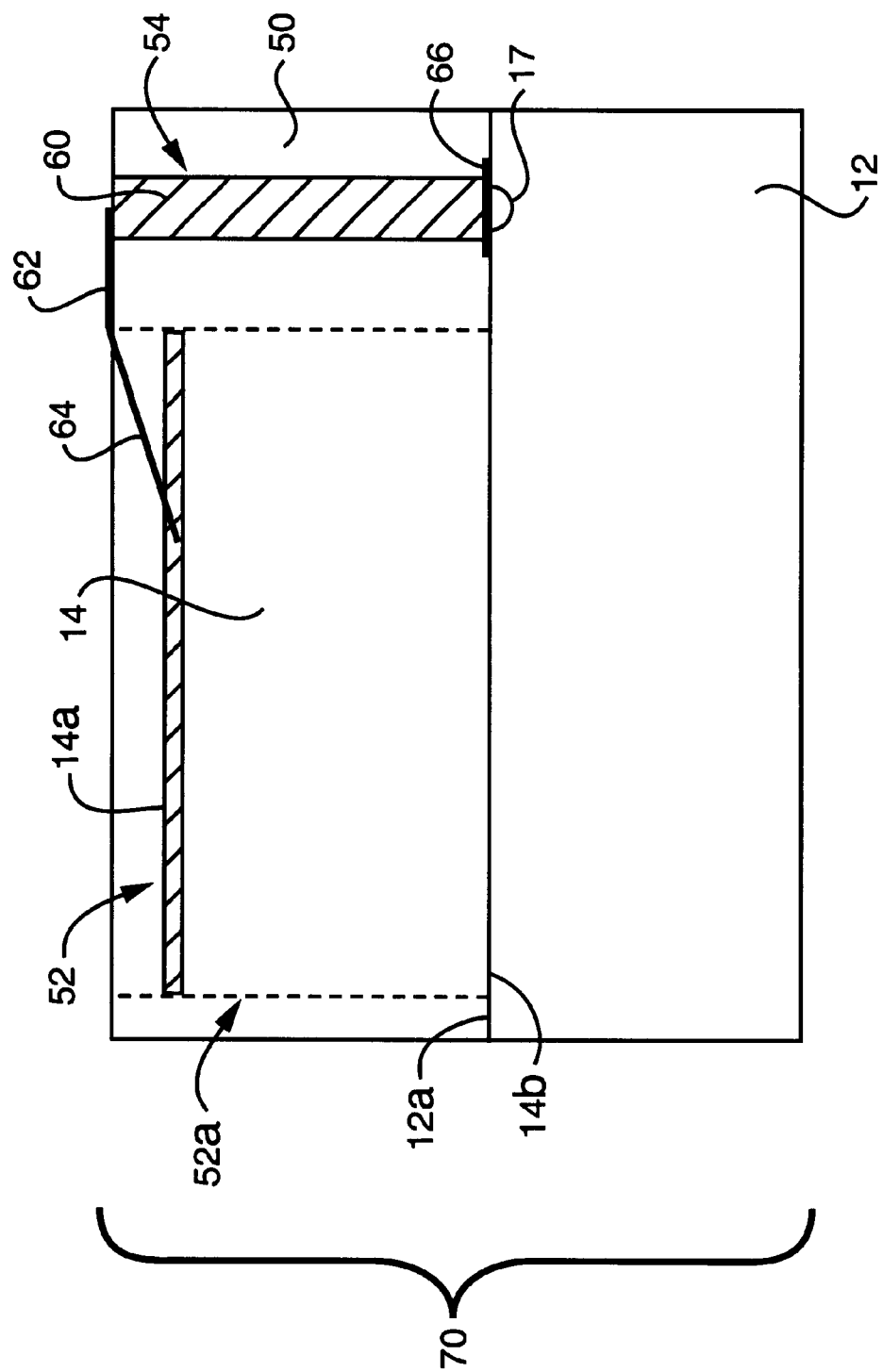
FIG. 7 is a side view of a portion of the photodiode array of FIG. 6.

FIG. 7 shows a detailed cross-sectional view of a single photodiode 14 mounted in a photodiode hole 52 of a portion of substrate 70. Since wire 19 is not used in the present invention there is no need to allow large gaps between each photodiode and the walls 52a of top piece 50 to accommodate traversal of the wire from the detection side 14a of photodiode 14 to a circuit path 17 (as required for grid 28 in the prior art array shown in FIG. 4). Therefore, the photodiode holes 52 may be smaller in dimension than the openings 26 in grid 28 of the prior art. Accordingly, the openings 26 in grid 24 are sized to align the scintillator crystals with photodiodes secured within photodiode holes 52. In the preferred embodiment, the array density of photodiodes and scintillator crystals within the X-ray detector is substantially the same as the prior art system of FIGS. 1–4. Therefore, grid 24 with openings 26 of the prior art may be used in the preferred embodiment. Top piece 50 provides physical protection and structural support for photodiodes 14 and provides improved alignment means of the photodiodes with the scintillator crystals 22. Insertion of photodiodes 14 into the top layer 50 allows photodiodes to be mounted directly to the bottom piece 12. In the preferred embodiment, each photodiode 14 is glued to the mounting surface 12a of bottom piece 12, using an electrically insulating adhesive, such as epoxy.

It is necessary that the height (or thickness) of top piece 50 be greater than the height of the photodiode 14. This configuration allows photodiodes to be mounted within the photodiode holes of substrate 70 such that a detection surface 14a of each photodiode 14 is countersunk relative to the top surface 50a of top piece 50. As a result, when the scintillator crystal array is coupled to top piece 50, each photodiode 14 is shielded by walls 52a, so is much less likely to receive light from surrounding scintillator crystals. That is, better optical isolation of the photodiodes is achieved. The countersinking of photodiodes 14 within photodiode holes 52 allows a relatively protected electrical path to be formed between detection side 14a of the photodiode and circuit path 17.

As will be appreciated from FIG. 7, the detection side 14a of a photodiode 14 may be electrically connected to conductive path 62 in a variety of ways. For example, an electrical coupling 64 such as a conductive wire (shown) or conductive epoxy may be used to electrically couple detection side 14a to path 62. In either case, because the photodiode 14 is countersunk in detector hole 52, the connection between detection side 14a and path 62 remains substantially protected within photodiode hole 52 and does not substantially interfere with a tight coupling of the array of scintillator crystals to the array of photodiodes at top piece 50. In the preferred embodiment, the conductive holes 54 are plated with an electrically conductive material 60 to provide an electrical path from the top surface 50a to the bottom surface 50b of top piece 50. Those skilled in the art will appreciate that an electrically conductive path within conductor holes 54 may be formed in a variety of ways. For example, the conductive holes 54 could be filled with a conductive epoxy or serve as a conduit for a metal plating. The top and bottom pieces 12 and 50 are fused together such that each conductive pad 66 on the bottom surface of the top piece becomes electrically coupled with a corresponding circuit path 17 of the bottom piece. Therefore, wire 64, path 62, plated conductive hole 60, and pad 66 form an electrical path from detection side 14a of a photodiode 14 to circuit path 17.

Figure 8:
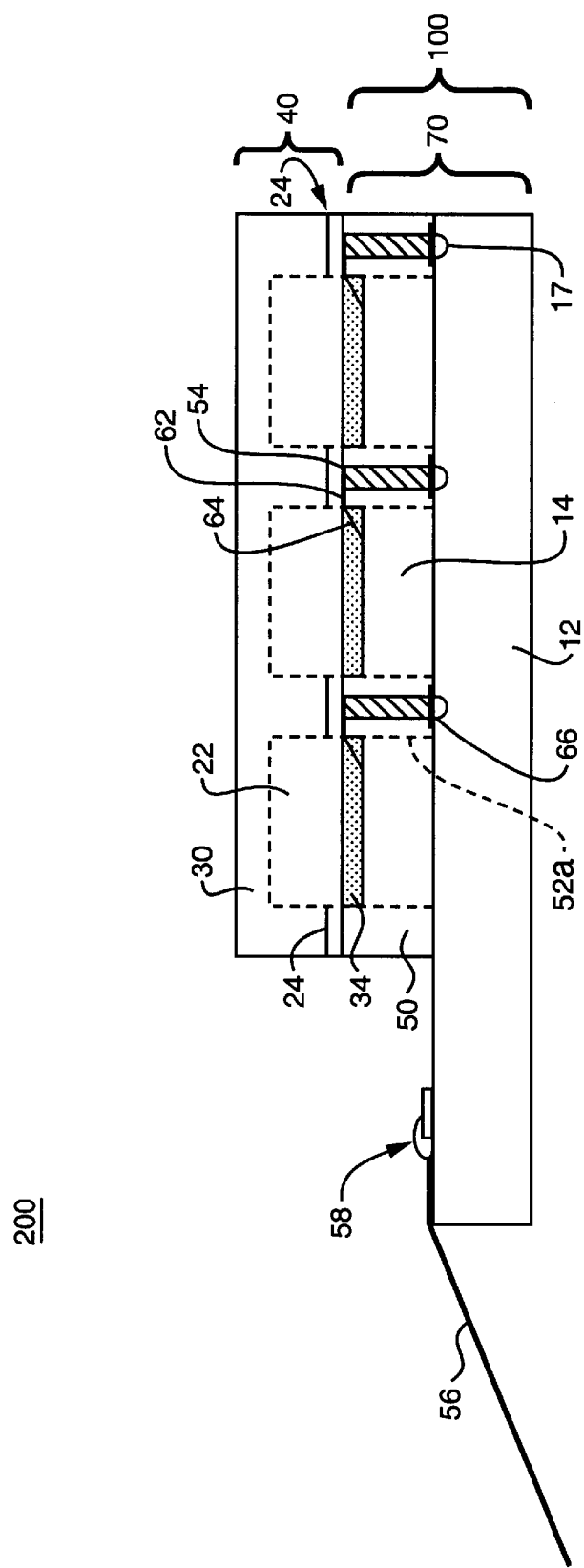
FIG. 8 is a side view of an X-ray detector array in accordance with the present invention.

FIG. 8 shows the preferred embodiment of an X-ray detector array 200 in accordance with the present invention. Detector array 200 includes a scintillator crystal array 40 coupled to a photodiode array 100. Photodiode array 100 includes the insulating substrate 70, formed from top piece 50 and bottom piece 12, and includes the photodiodes 14 subsequently mounted within photodiode holes 52 and glued to mounting surface 12a of the bottom piece, as previously discussed. The scintillator crystal array 40 is substantially that of the prior art, and includes the prior art alignment grid 24 and scintillator crystals 22 secured within a reflective substrate 30 made from an optically reflective material. The recess defined by the detection surface 14a of the photodiode 14 and the walls of the detector hole 52, i.e., the unoccupied volume of the detector hole 52, is filled with an optically transparent substance (e.g., optical epoxy or gel). In the preferred embodiment, the optically transparent substance is an optical epoxy 34, which allows the light to propagate from the scintillator crystal 22 to the detection surface 14a of photodiode 14. The optical epoxy also fills in any existing gaps between the sides of the photodiode 14 and walls 52a of photodiode hole 52. Once the optical epoxy 34 is in place, the scintillator array (including scintillating crystals 22, reflective substrate 30, alignment grid 24), and substrate 70 (with photodiodes mounted therein) are bonded together to from the X-ray detector 200.

When X-rays impinge on the scintillator crystals 22, the crystals produce light. The photodiodes 14 receive the light and generate corresponding electrical signals proportional to the emitted light, thus proportional to the original X-ray flux received. For each photodiode, these electrical signals are transmitted via electrical 64 and pad 62 to a plated conductive hole 60 and then to circuit path 17. Each signal is propagated through a circuit path 17 to the multiwire flex cable 56 and ultimately to the electronics, which process signals from the photodiodes in accordance with known algorithms to determine, inter alia, the density distribution in an object scanned by a CT scanner.

The novel construction of the photo-detector array and the X-ray detector provides improved optical separation between photodiodes without requiring the use of the fragile expensive glass grid 28 of the prior art. The construction also ensures better protection for the photo-detectors because of the improved structural support provided by the top piece, eliminates the risk of bond stress at points along the electrical path between the photodiode detection surface and the circuit path, and simplifies bonding execution by eliminating the labor intensive physically restrictive installation of the wire leads. Consequently, X-ray detection accuracy is preserved and the manufacturing is simplified and associated costs reduced.

The invention may be embodied in other specific forms without departing from the spirit or central characteristics thereof. The present embodiments are, therefore, to be considered in all respects as illustrative and not restrictive, the scope of the invention being indicated by appending claims rather than by the foregoing description, and all changes that come within the meaning and range of equivalency of the claims are therefore intended to be embraced therein.

What is claimed is:

1. A 2-D mounting substrate, within which photo-detectors of an X-ray detector system are mountable, the mounting substrate comprising:
   a. a framework defining a 2-D array of substantially optically isolated photo-detector holes formed within said framework, each photo-detector hole being dimensioned to receive a single photo-detector and to align said photo-detector with a corresponding scintillating element of a corresponding scintillator element array, wherein the photo-detector holes have a height greater than the height of a photo-detector; and
   b. a corresponding array of electrically conductive and mutually isolated circuit paths, wherein a different pair of circuit paths corresponds to each of the photo-detector holes and connects to a photo-detector mounted therein.

2. The 2-D mounting substrate of claim 1, wherein the substrate is comprised of an optically opaque material.

3. The 2-D mounting substrate of claim 1, wherein the substrate is comprised of:
   a. a top piece, having a top surface and a bottom surface and wherein the photo-detector holes are formed in the top piece and extend from the top surface to the bottom surface; and
   b. a bottom piece, having a mounting surface which includes the circuit paths and to which the bottom surface of the top piece is rigidly coupled.

4. The 2-D mounting substrate of claim 3, wherein the top piece and bottom piece are substantially comprised of optically opaque, nonconductive material and coupled by a thermal-pressure joining process.

5. The 2-D mounting substrate of claim 3, wherein the top piece has a height greater than the height of a photo-detector.

6. The 2-D mounting substrate of claim 3, further including conductive holes formed within the top piece, wherein at least two conductive holes correspond to a photo-detector hole and each provides an electrical path through the top piece and wherein each conductive hole is electrically coupled to a different circuit path on said bottom piece.

7. The 2-D mounting substrate of claim 6, wherein each conductive hole is plated with a conductive material.

8. The 2-D mounting substrate of claim 6, wherein each photo-detector is electrically coupled to the at least two corresponding conductive holes via corresponding electrically conductive and mutually isolated paths formed at the top surface of the top piece.

9. The 2-D mounting substrate of claim 6, wherein the bottom surface of the top piece includes, electrically coupled to each conductive hole, a corresponding conductive pad which provides an electrical coupling of said conductive hole to a corresponding one of said plurality of electrically isolated circuit paths.

10. The 2-D mounting substrate of claim 3, wherein the area of the bottom surface of the top piece is smaller than the area of the mounting surface of the bottom piece, wherein an exposed area of the mounting surface is defined when the top and bottom pieces are rigidly coupled together, and wherein the exposed area of the mounting surface of the bottom piece includes a plurality of separate bonding pads, one pad being electrically coupled to each circuit path.

11. An X-ray detector array, comprising:
   a. an array of scintillator elements secured within a substantially rigid optically reflective structure, wherein each scintillator element emits light in response to the incidence of X-rays thereon;
   b. an optically opaque photo-detector substrate, including:
      i. a framework defining a 2-D array of photo-detector holes formed within said framework, each photo-detector hole being dimensioned to receive a single photo-detector and to align said photo-detector with a corresponding scintillating element in the array of scintillator elements, wherein the photo-detector holes have a height greater than the height of a photo-detector; and
      ii. a corresponding array of electrically conductive and mutually isolated circuit paths, wherein a different pair of circuit paths corresponds to each of the photo-detector holes and connects to a photo-detector mounted therein; and
   c. a plurality of photo-detectors, wherein each photo-detector is countersunk within a corresponding one of the photo-detector holes and is electrically coupled to a pair of different circuit paths and is optically coupled to a corresponding scintillator element when the array of scintillator elements is coupled to the photo-detector substrate.

12. The X-ray detector array of claim 11, wherein the scintillator elements are chosen from a group including scintillating crystals, scintillating ceramics, and direct conversion materials including Cadmium Telluride and Selenium.

13. The X-ray detector array of claim 11, wherein the photo-detectors are chosen from a group including photodiodes, charge-coupled devices, mono-crystalline silicon devices, and amorphous silicon devices.

14. The X-ray detector array of claim 11 further comprising an alignment grid, wherein the alignment grid has an array of openings formed therein and further aligns each scintillator element with its corresponding photo-detector.

15. The X-ray detector array of claim 11, wherein the substrate is comprised of:
   a. a top piece, having a top surface and a bottom surface and wherein the photo-detector holes are formed in the top piece and extend from the top surface to the bottom surface; and
   b. a bottom piece, having a mounting surface which includes the circuit paths and to which the bottom surface of the top piece is rigidly coupled.

16. The X-ray detector array of claim 15, wherein the top piece and bottom piece are substantially comprised of optically opaque materials and coupled by a thermal-pressure joining process.

17. The X-ray detector array of claim 15, wherein the top piece has a height greater than the height of a photo-detector.

18. The X-ray detector array of claim 15, further including conductive holes formed with the top piece, wherein at least two conducive holes correspond to a photo-detector hole and each provides an isolated electrical path through the top piece and wherein each conductive hole is electrically coupled to a different circuit path on said bottom piece.

19. The X-ray detector array of claim 18, wherein each conductive hole is plated with a conductive material.

20. The X-ray detector array of claim 18, wherein each photo-detector hole is electrically coupled to the at least two a corresponding conductive holes via corresponding electrically conductive and mutually isolated paths formed at the top surface of the top piece.

21. The X-ray detector array of claim 20, wherein each photo-detector is electrically coupled to its corresponding conductive paths with an electrically conductive epoxy or wire bonded.

22. The X-ray detector array of claim 20, wherein the bottom surface of the top piece includes, electrically coupled to each conductive hole, a corresponding conductive pad which provides an electrical coupling of said conductive hole to a corresponding one of said plurality of electrically isolated circuit paths.

23. The X-ray detector array of claim 15, wherein the area of the bottom surface of the top piece is smaller than the area of the mounting surface of the bottom piece, wherein an exposed area of the mounting surface is defined when the top and bottom pieces are rigidly coupled together, and wherein the exposed area of the mounting surface of the bottom piece includes a plurality of separate bonding pads, one pad being electrically coupled to each circuit path.

24. A CT scanning system including a radiation source, means for detecting radiation emitted from said source and providing signals representative of the detected radiation, means for moving said source and said detecting means about and relative to an object to be scanned, means for supplying power to said radiation source, and means for processing said signals to acquire image data relating to said object being scanned, and a 2-D detector array, comprising:
  a. an array of scintillator elements secured within a substantially rigid optically reflective structure, wherein each scintillator element emits light in response to the incidence of X-rays thereon;
  b. an optically opaque photo-detector substrate, including:
     i. a framework defining a 2-D array of photo-detector holes formed within said framework, each photo-detector hole being dimensioned to receive a single photo-detector and to align said photo-detector with a corresponding scintillating element in the array of scintillator elements, wherein the photo-detector holes have a height greater than the height of a photo-detector; and
     ii. a corresponding array of electrically conductive and mutual isolated circuit paths, wherein a different pair of circuit paths corresponds to each of the photo-detector holes and connects to a photo-detector mounted therein; and
  c. a plurality of photo-detectors, wherein each photo-detector is countersunk within a corresponding one of the photo-detector holes and is electrically coupled to at least one different circuit path and is optically coupled to a corresponding scintillator element when the array of scintillator elements is coupled to the photo-detector substrate.

25. The CT scanning system of claim 24, wherein:
the scintillator elements are chosen from a group including scintillating crystals, scintillating ceramics, and direct conversion materials including Cadmium Telluride and Selenium; and the photo-detectors are chosen from a group including photodiodes, charge-coupled devices, of monocrystalline silicon devices, and amorphous silicon devices.

26. The CT scanning system of claim 24 further comprising an alignment grid, wherein the alignment grid has an array of openings formed therein and aligns each scintillator element with its corresponding photo-detector.

27. The CT scanning system of claim 24, wherein the substrate is comprised of:
  a. a top piece, having a top surface and a bottom surface and wherein the photo-detector holes are formed in the top piece and extend from the top surface to the bottom surface; and
  b. a bottom piece, having a mounting surface which includes the circuit paths and to which the bottom surface of the top piece is rigidly coupled.

28. The CT scanning system of claim 27, wherein the top piece and bottom piece are substantially comprised of optically opaque ceramic and joined by a thermal-pressure joining process.

29. The CT scanning system of claim 27, wherein the top piece has a height greater than the height of a photo-detector.

30. The CT scanning system of claim 27, further including conductive holes formed within the top piece, wherein at least two conductive holes corresponds to a photo-detector and each provides an isolated electrical path through the top piece and wherein each conductive hole is electrically coupled to a different circuit path on said bottom piece.

31. The CT scanning system of claim 30, wherein each conductive hole is plated with a conductive material.

32. The CT scanning system of claim 30, wherein each photo-detector hole is electrically coupled to the at least two corresponding conductive holes via a corresponding electrically conductive and mutually isolated path formed at the top surface of the top piece.

33. The CT scanning system of claim 32, wherein each photo-detector is electrically coupled to its corresponding conductive paths with an electrically conductive epoxy or wire bonding.

34. The CT scanning system of claim 32, wherein the bottom surface of the top piece includes, electrically coupled to each conductive hole, a corresponding conductive pad which provides an electrical coupling of said conductive hole to a corresponding one of said plurality of electrically isolated circuit paths.

35. The CT scanning system of claim 27, wherein the area of the bottom surface of the top piece is smaller than the area of the mounting surface of the bottom piece, wherein an exposed area of the mounting surface is defined when the top and bottom pieces are rigidly coupled together, and wherein the exposed areas of the mounting surface of the bottom piece includes a separate bonding pad electrically coupled to each circuit path.

* * * * *